US005840587A

United States Patent [19]
Stewart et al.

[11] Patent Number: 5,840,587
[45] Date of Patent: Nov. 24, 1998

[54] METHODS FOR DETERMINING ANTIPHOSPHOLIPID ANTIBODIES

[75] Inventors: Michael W. Stewart, Albert; Phillip A. Gordon; Wai Sum Etches, both of Edmonton, all of Canada

[73] Assignee: University Hospitals Board, Edmonton, Canada

[21] Appl. No.: 477,334

[22] Filed: Jun. 7, 1995

Related U.S. Application Data

[62] Division of Ser. No. 129,593, Sep. 30, 1993, Pat. No. 5,561,070, which is a division of Ser. No. 905,562, Jun. 29, 1992, abandoned.

[30] Foreign Application Priority Data

Jun. 26, 1992 [CA] Canada ................................... 2072548

[51] Int. Cl.$^6$ .................................................. C01N 33/563
[52] U.S. Cl. ........................... 436/513; 356/73; 356/336; 356/343; 435/7.92; 435/7.94; 435/973; 436/512; 436/513; 436/518; 436/523; 436/526; 436/528; 436/531; 436/534; 436/52; 436/800; 436/805
[58] Field of Search ............................ 356/73, 336, 343; 435/7.92, 7.94, 973; 436/512, 513, 518, 523, 526, 528, 531, 534, 52, 800, 805

[56] References Cited

U.S. PATENT DOCUMENTS

| | | | |
|---|---|---|---|
| 4,597,999 | 7/1986 | Lingwood | 427/54.1 |
| 4,738,932 | 4/1988 | Yabusaki | 435/7.36 |
| 4,828,996 | 5/1989 | Siegel | 435/177 |
| 5,162,863 | 11/1992 | Ito | 356/73 |
| 5,344,758 | 9/1994 | Krillis et al. | 435/7.1 |

OTHER PUBLICATIONS

Harris, E.N., "Evaluation of the anti–cardiolipin antibody test: report of an international workshop held 4 Apr. 1986", Clin. Exp. Immunol., 68: 215–222 (1987).

Harlow et al., "Antibodies: A Laboratory Manual," Cold Spring Harbor Laboratory, (1988), pp. 626–627.

E. Nigel Harris et al., "Use of Enzyme–Linked Immunosorbent Assay and of Inhibition Studies to Distinguish Between Antibodies to Cardiolipin from Patients with Syphilis or Antoimmune Disorders", J. Infect. Diseases 157 (1):23–31 (1988).

Al–Momen, A.K., et al, "IgA Antiphospholipid and Adrenal Insufficiency: is There a Link?", Thromb. Res. 64: 571 (1991).

Quamar, T. et al., "Characteristics of High–Titer IgG Antiphopholipid Antibody in Systemic Lupus Erythematosus Patients with and without Fetal Death", Arthritis Rheum. 33 (4): 501 (1990).

Pirruccello, S.J. et al., "Cardiolipin Liposomes: A Novel Flow reagent for Detection of Anticardiolipin Antibodies", J. Clinical Lab. Annal. 4: 236 (1990).

Kedar, A., et al., "Lipid Coating of Paramagnetic Microspheres" in Bone and Marrow Purging and Processing, Alan R. Liss, pp. 293–301 (1990).

Gilmann–Sachs, A., et al., "Patterns of Antiphospholipid Antibodies", J. Clin. Lab. Immunol. 35: 83–55 (1991).

Tiissen, Practice and Theory of Enzyme Immunoassays, vol. 15, Laboratory Techniques in Biochemistry and Molecular Biology, N. Y., Elsevier, pp. 311–314 (1985).

Stewart, M.W., et al., "Detection of Antiphospholipid Antibodies", Thrombosis & Haemostasis 70(4): 603–607 (1993).

*Primary Examiner*—Susan Wolski
*Attorney, Agent, or Firm*—Viviana Amzel; Pretty, Schroeder and Poplawski

[57] ABSTRACT

The invention provides phospholipid coated particles capable of specifically binding antiphospholipid antibodies and a method for preparing such particles. Methods are also provided for determining antiphospholipid antibodies in a serum or plasma. Also provided are methods for isolating antiphospholipid antibodies from a fluid and for raising specific antiphospholipid antibodies.

25 Claims, 7 Drawing Sheets

|           |     | PI   | PS   | CL   |
|-----------|-----|------|------|------|
| Patient 1 | IgG | Med  | Med  | High |
|           | IgM | Med  | High | High |
|           | IgA | Neg  | Low  | Med  |
| Patient 2 | IgG | Med  | Med  | High |
|           | IgM | High | Low  | Med  |
|           | IgA | Low  | Neg  | Low  |
| Patient 3 | IgG | Med  | High | High |
|           | IgM | Med  | Med  | Med  |
|           | IgA | Neg  | Neg  | Neg  |
| Patient 4 | IgG | Low  | Neg  | Low  |
|           | IgM | Low  | Neg  | Neg  |
|           | IgA | Neg  | Neg  | Neg  |
| Patient 5 | IgG | Neg  | Neg  | Neg  |
|           | IgM | Med  | Neg  | Low  |
|           | IgA | Low  | Neg  | Neg  |
| Patient 6 | IgG | Neg  | Neg  | Low  |
|           | IgM | Med  | Low  | Low  |
|           | IgA | Neg  | Neg  | Neg  |
| Patient 7 | IgG | Neg  | Neg  | Med  |
|           | IgM | Med  | Low  | Low  |
|           | IgA | Neg  | Neg  | Neg  |

FIG.6

METHODS FOR DETERMINING ANTIPHOSPHOLIPID ANTIBODIES

This application is a divisional of U.S. Ser. No. 08/129,593, filed Sep. 30, 1993, now U.S. Pat. No. 5,361,070, which is a divisional of U.S. Ser. No. 07/905,562, filed Jun. 29, 1992, which is now abandoned.

BACKGROUND

This invention relates to methods for detecting and measuring antibodies to phospholipids.

Antibodies to phospholipids have been implicated in a variety of diseases or clinical conditions including arterial and venous thrombosis, recurrent fetal loss, thrombocytopenia, pulmonary embolism, coronary thrombosis, cerebral thrombosis, livedo reticularis and HIV infection.

It is therefore important to have a convenient and reproducible clinical method for detecting and measuring antiphospholipid antibodies in samples from patients.

A variety of phospholipids can give rise to antibodies in humans and antibodies specific to cardiolipin, phosphatidylinositol, phosphatidylserine and phosphatidylethanolamine, for example, have been found.

Not all of these antibodies are necessarily present in every disease associated with anti-phospholipid antibodies. It is therefore desirable to be able to determine easily antibodies to various specific phospholipids.

Furthermore, antibodies to a particular phospholipid may be IgG, IgM or IgA type immunoglobulins and not all types may be present in all conditions; for example, IgA antibodies have been linked to adrenal insufficiency (Al-Momen et al., (1991), Thromb. Res., Vol 64, p. 571) and high levels of IgG antiphospholipid antibodies have been noted in systemic lupus erythematosus (Quamar, T. et al., (1990), Arthritis Rheum, Vol 33, p. 501).

It is therefore desirable to be able to distinguish antibodies of several immunoglobulin classes.

Presently available commercial methods for determining antiphospholipid antibodies are based on enzyme-linked immunosorbent assays (ELISA). Commercially available kits use cardiolipin as substrate and therefore detect only anti-cardiolipin antibodies.

Radioimmunoassays have also been used to measure anti-phospholipid antibodies but these have all the drawbacks associated with the use of radioactive materials.

A flow cytometric assay has also been reported for determining anti-cardiolipin antibodies (Pirruccello et al; (1990), J. Clin. Lab. Anal., vol. 4, p. 236). This assay utilises liposomes as carriers of the phospholipids. The difficulty of controlling liposome size makes standardization of the liposomes a problem. In addition, liposomes are generally composed of more than one phospholipid to lend stability to the liposome.

The methods presently available for determination of antiphospholipid antibodies are limited in their flexibility and convenience, particularly when one considers the increasing clinical need for determination of antibodies of different immunoglobulin classes and specific to particular phospholipids.

SUMMARY OF THE INVENTION

In accordance with one aspect of the invention, a method is provided for determining antiphospholipid antibodies in a fluid comprising the steps of:

(a) providing phospholipid coated particles coated with at least one phospholipid for which antibodies are to be determined;

(b) contacting the fluid with the coated particles to permit binding of the antibodies to the particles; and (c) determining the antiphospholipid antibodies bound to the particles.

In accordance with a further aspect of the invention, a method is provided for isolating from a fluid antibodies to a phospholipid the method comprising:

(a) contacting the fluid with phospholipid coated particles wherein the phospholipid is that for which antibodies are to be isolated, to permit binding of the antibodies to the particles;

(b) separating the particles from the residual solution;

(c) recovering the anti-phospholipid antibodies from the particles.

In accordance with a further aspect of the invention, a method is provided for producing antiphospholipid antibodies specific to a phospholipid comprising providing particles treated with the phospholipid to permit binding of the phospholipid to the particles and injecting the treated particles subcutaneously into a suitable animal.

In accordance with a further aspect of the invention, a method is provided for preparing phospholipid coated particles comprising:

(a) contacting particles with a solution of a phospholipid at an effective temperature to permit binding of the phospholipid to the particles; and (b) contacting the particles with a blocking agent at an effective temperature to permit blocking of non-specific binding sites on the particles.

In accordance with a further aspect of the invention, particles are provided which are coated with at least one phospholipid, the coated particles being able to bind specifically antibodies to the at least one phospholipid.

SUMMARY OF DRAWINGS

The invention, as exemplified by preferred embodiments, is described with reference to the drawings in which:

FIG. 6 shows antiphospholipid antibody levels in seven patients.

DETAILED DESCRIPTION OF THE INVENTION

Figure 1:
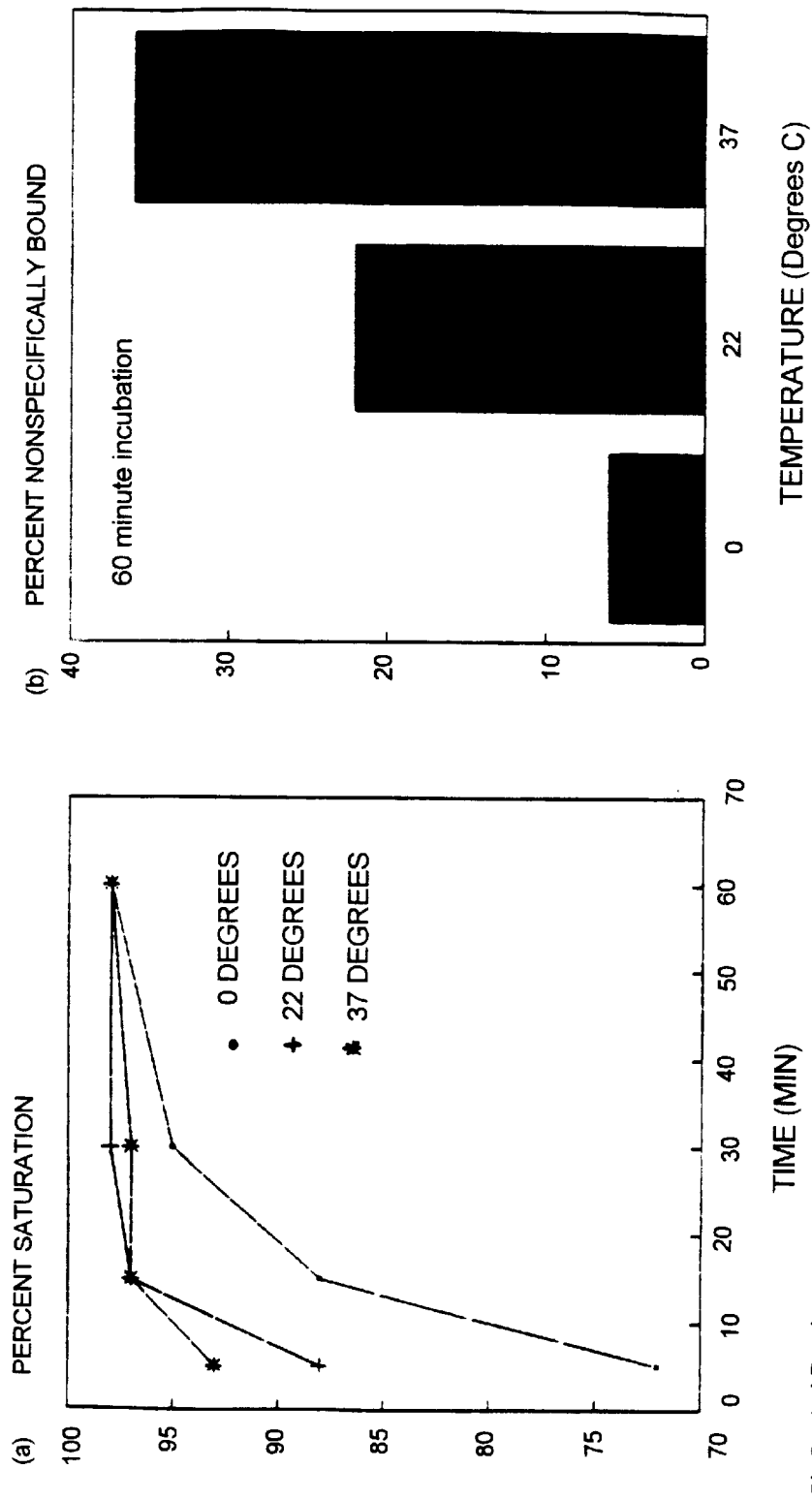
FIG. 1 shows: (a) the time course of antibody binding and (b) the effect of temperature on non-specific binding.
Figure 2:
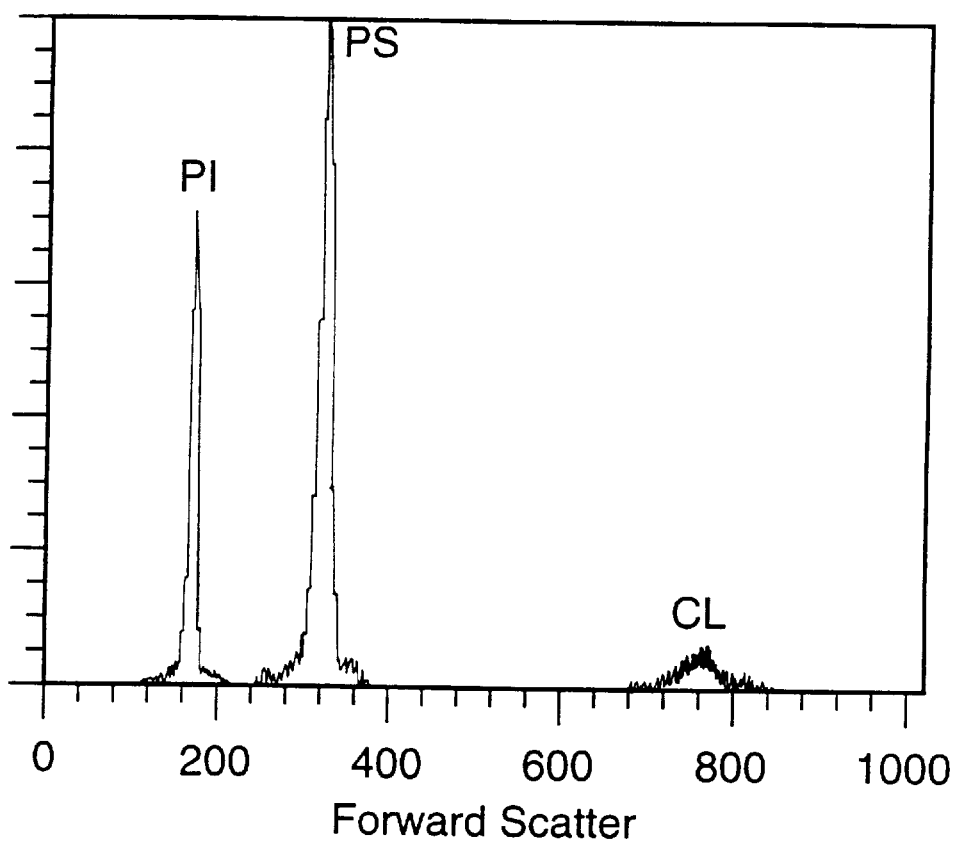
FIG. 2 is a scatter histogram showing bead size discrimination by flow cytometry.

In accordance with a first embodiment, the subject invention provides novel phospholipid coated particles which show specific binding of antiphospholipid antibodies, are easily prepared, stable and can be conveniently manipulated and employed in a variety of methods for determining antiphospholipid antibodies. The versatility of the phospholipid coated particles of the invention provides assays which can conveniently identify antiphospholipid antibodies of different classes and different phospholipid specifities, and provides for quantitation of these antibodies, by methods which are reproducible and sensitive and suitable for clinical diagnostic purposes.

In accordance with a further embodiment of the invention, a method is provided for preparing such phospholipid coated particles, for example microspheres or beads.

The inventors have found that polystyrene microspheres or beads can unexpectedly be coated with a phospholipid by relatively gentle techniques. Although microspheres coated with proteins have previously been described, the hydrophobic nature of phospholipids makes it difficult for these to stick to the charged microsphere surface.

In accordance with a preferred embodiment, polystyrene microspheres are treated with a solution of the desired phospholipid in ethanol in the dark for at least about twelve hours at an effective temperature, to permit binding of the phospholipid. In an especially preferred embodiment, phospholipid treatment is carried out at a temperature in the range of about 0° to about 4°. As will be appreciated by those skilled in the art, the microspheres can be coated with phospholipid at higher temperatures but as the treatment temperature is raised above about 4° C., there is increasing damage to phospholipid molecules so that when the coated microspheres are used for assay of antiphospholipid antibodies, as will be described, less than optimal results are obtained; for example, coating of the microspheres with phospholipid at 22° C. produces broad peaks on flow cytometry and reduces specificity and sensitivity of the assay.

After treatment with phospholipid, the microspheres can be employed to raise specific antiphospholipid antibodies as will be described. The microspheres can also be stored at this stage, as described in Example 1.

When the microspheres are to be employed for determination of antiphospholipid antibodies or for isolation of antibodies, they are treated with a blocking agent to reduce non-specific binding of immunoglobulins and other potentially interfering proteins. In accordance with a preferred embodiment, the microspheres are treated with 10% fetal calf serum as blocking agent for about 15 to about 60 minutes at a temperature in the range of about 4° C. to about 37° C. It is especially preferred to carry out blocking at about 37° C. as this gives the lowest levels of non-specific binding when the microspheres are used to determine antiphospholipid antibodies. Blocking at lower temperatures tends to increase the level of non-specific binding to the microspheres in the assay.

The phospholipid coated microspheres are generally cooled after blocking treatment to a temperature of about 0° C. to about 4° C., since this is the temperature range at which they are optimally stored or employed in the antiphospholipid antibody assay.

It is believed that the incubation of the phospholipid treated beads with the blocking agent at an elevated temperature renders the phospholipid more mobile about the surface of the bead, resulting in efficient exposure of the bead surface sites responsible for non-specific binding of proteins. The rapid cooling may render the phospholipid less mobile about the bead, effectively locking the phospholipid molecules in place, with the majority of the nonspecific binding sites blocked.

In this specification, the terms 'coated particles', 'phospholipid coated particles', 'coated microspheres or beads' and the like are used to mean particles, microspheres or beads coated with phospholipid and treated with blocking agent. Where particles, microspheres or beads with bound phospholipid but without blocking treatment are referred to, this is specifically indicated.

Polystyrene microspheres are obtainable in a variety of sizes and are preferred for preparation of the phospholipid coated particles of the invention. Other suitable solid particulate supports will be known to those skilled in the art and include particles of suitable shape composed of a material capable of holding a charge such as polypropylene, polyethylene, acrylonitrile, polycarbonate or nitrocellulose or magnetic beads. The shape of the particle should be compatible with the needs of the method ultimately employed to determine antiphospholipid antibodies once these are bound to the phospholipid coated particle. For example, if flow cytometry is to be employed, the particles should be generally spherical. The size of particle employed should also be suitable for the detection method to be employed. For example, microspheres of diameter from about 0.8 $\mu$m to about 10 $\mu$m are suitable for flow cytometry whereas larger or smaller particles may be required for other assay techniques e.g., around 0.06 $\mu$m diameter for latex enhanced laser nephelometry or around 15 $\mu$m for latex bead agglutination.

Adult bovine serum has also been found to be suitable as blocking agent for work with antiphospholipid antibodies, as described by Harris et al. (Clin, Exp. Immunol. (1987), vol. 68, p. 215) whereas certain other proteins are unsuitable. A suitable blocking agent should provide low levels of non-specific binding when the microspheres are used for antiphospholipid antibody assay.

One of the advantages of using microspheres such as polystyrene microspheres as particulate supports to prepare phospholipid coated particles is their availability in a variety of sizes.

In accordance with a further embodiment of the invention, microspheres of different sizes are selected and each size of microspheres is coated with a different phospholipid, followed by treatment with blocking protein, as described in Example 1.

The coated microspheres may be easily distinguished by virtue of their size differences, allowing for rapid differentiation of antibodies to different phospholipids, as will be described. As will be understood by those skilled in the art, microspheres of a single size may be coated with a mixture of phospholipids but this will provide for assay of total antiphospholipid antibodies only and not for any differentiation.

The phospholipid coated microspheres of the invention provide a convenient antigen-presenting device which may be employed along with a variety of detection procedures to detect and to determine antiphospholipid antibodies.

In accordance with a further preferred embodiment of the invention, a method is provided for detecting and measuring antiphospholipid antibodies in a fluid such as human serum or plasma. Serum or plasma is incubated with the phospholipid coated microspheres of the invention at an effective temperature to allow binding of the antiphospholipid antibodies. The microspheres are then contacted with a secondary antibody directed against human immunoglobulins, this secondary antibody bearing a suitable detectable label, whereby detection and quantitation of the label permits detection and quantitation of the bound antiphospholipid antibodies.

Incubation of sera with phospholipid coated microspheres of the invention at various temperatures showed that as the temperature of incubation is increased, non-specific binding of the secondary antibody also is increased, as seen in FIG. 1, panel B. In accordance with a preferred embodiment, the incubation is carried out at a temperature in the range of about 0° C. to about 22° C. An especially preferred range is about 0° C. to about 4° C., in which range the non-specific binding is at a minimum.

At 0° C., the binding reaction approaches saturation at about 30 minutes, as seen in FIG. 1, panel A. Saturation is reached more quickly at higher temperatures.

The preferred pH range for binding of serum antiphospholipid antibodies to the phospholipid coated beads of the invention is about pH 6.8 to about pH 7.8. A pH range of about 7.2 to about 7.4 is especially preferred.

Icteric and haemolysed serum samples may be assayed by the method of the invention without problems.

As will be understood by those skilled in the art, a variety of techniques may be used in the determination of the secondary labelled antibody, including flow cytometry, latex bead agglutination, fluorescence microscopy, latex bead enhanced laser nephelometry and immuno-dot blotting.

In accordance with a preferred embodiment of the invention, a rapid screening method is provided for detection of antiphospholipid antibodies in human serum.

Separate portions of microspheres are each coated with one phospholipid to which antibodies are to be detected. The microspheres coated with different phospholipids are mixed and incubated with serum as described in Example 3.

A polyvalent secondary antibody reacting with IgG, IgM and IgA and bearing a suitable label, e.g., FITC, is added in excess, without separation of the microspheres from the serum. The mixture is incubated for 30 minutes at room temperature in the dark then diluted 30-fold with saline and analysed directly in a flow cytometer, without separation of the microspheres from the incubation mixture. Immune complexes between the immunoglobulins of the test serum and the secondary antibody are present but are much smaller than the microspheres and can be excluded by electronic gating during the flow cytometer analysis, as will be understood by those skilled in the art.

The fluorescence emitted by the microspheres having bound secondary antibody is detected and indicates the presence of antiphospholipid antibodies in the test serum to any or all of the phospholipids which were used to coat the beads. If desired, the amount of fluorescence will provide a semi-quantitative assessment of the antiphospholipid antibodies present, if appropriate standard curves are prepared.

In accordance with a further preferred embodiment of the invention, a screening method is provided for detection and identification of specific antiphospholipid antibodies in human serum.

Phospholipid coated microspheres of three sizes, coated respectively with phosphoinositol, (PI) phosphatidylserine (PS) and cardiolipin (CL), as described in Example 1, are incubated with serum as described in Example 2. The microspheres are separated from the serum and incubated with a cocktail of secondary antibodies containing anti-human IgG F(ab')$_2$ linked to FITC, anti-human IgM linked to phycoerythrin (PE) and anti-human IgA linked to biotin. Secondary antibodies are titrated to be saturating and incubation is carried out at room temperature in the dark for 15 to 60 minutes depending on the degree of saturation. Unbound secondary antibody is removed by centrifugation and the microspheres are resuspended in saturating avidin linked to PE/Texas Red and incubated in the dark at room temperature for 15 minutes, to allow binding to the IgA-linked biotin.

The microspheres are then separated by centrifugation and resuspended in an iso-osmolar salt solution such as ISOTON II™ suitable for flow cytometry.

Flow cytometric analysis is conducted as in Example 2. The detected antiphospholipid antibodies can be identified as anti-PI, anti-PS and anti-CL and classified as IgA, IgG or IgM. If desired, the amount of fluorescence will provide a semi-quantitative assessment of the antiphospholipid antibodies present, if appropriate standard curves are prepared.

As will be appreciated by those skilled in the art, this screening procedure may be carried out using microspheres coated with other phospholipids, as desired. Furthermore, the procedure is not limited to three sizes of microspheres, thereby providing a screen for three types of phospholipid. Additional sizes of microspheres with additional phospholipids may be employed, as permitted by the discriminatory capabilities of the flow cytometer used.

It has, however, been found convenient to use three sizes of microspheres of diameters as described in Example 1, as these sizes may be examined simultaneously within the detection limits of the flow cytometer.

The different size classes of coated beads are mixed in proportions such that the surface area presented by each population to the test serum was the same.

It has been found that when whole molecule IgG is used as secondary antibody, either alone or in a cocktail with other antibodies, non-specific binding tends to be high and interferes with the flow cytometric analysis. For determination of IgG antibodies, it is preferred to use the F(ab')$_2$ fragment of human IgG as secondary antibody.

Human serum may be screened first by the rapid method to eliminate negatives before screening to identify particular antiphospholipid antibodies or may be screened directly with the more discriminating screening procedure.

Other suitable detectable labels for the second antibodies will be known to those skilled in the art and include fluorescent compounds such as fluoresceins, rhodamines, erythrosin, phycoerythrin, phycoerythrin/Texas red conjugate, Texas red and propidium iodide. For assays such as immunodot blot, lables such as peroxidase, alkaline phosphatase and ferritin may be used.

In accordance with a further embodiment of the invention, a method is provided for quantitation of antiphospholipid antibodies in human serum.

For optimal quantitation of antiphospholipid antibodies, it is preferred to use phospholipid coated microspheres of one size and phospholipid type and to use secondary antibody of one immunoglobulin class labelled with a convenient fluorophore such as FITC or PE in the method of the invention.

Standard curves are prepared using commercially available antiphospholipid antibody standards incubated with microspheres coated with the appropriate phospholipid and then reacted with known amounts of the appropriate immunoglobin class as secondary antibody, as described in Example 4.

Sera from patients presenting with thrombotic tendencies have been analysed by the method of the invention and antiphospholipid antibodies have been detected in over half of them.

Figure 7:
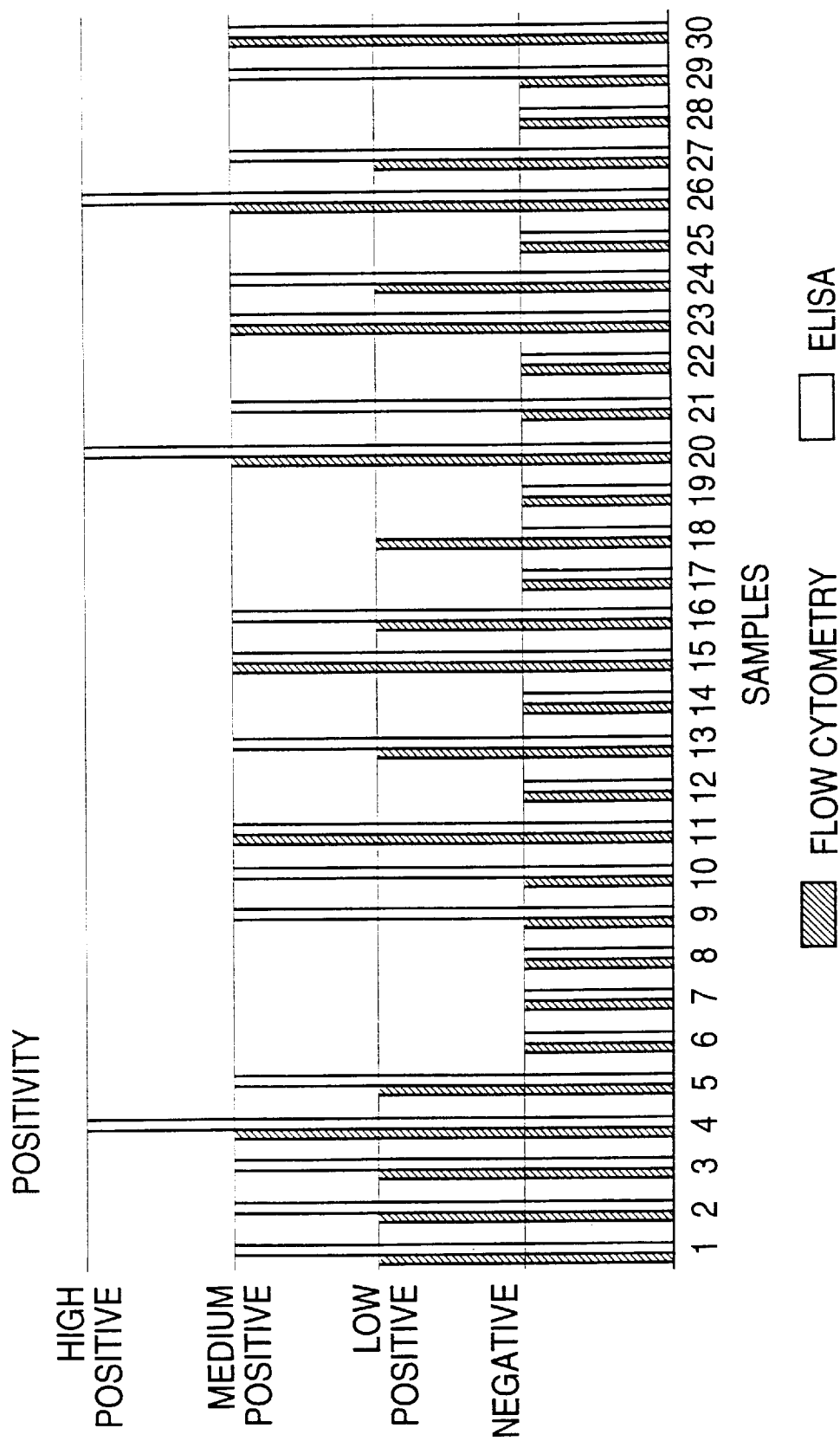
FIG. 7 shows a comparison of serum anticardiolipin antibody levels determined by ELISA and by the method of the invention.

The serum levels of anti-cardiolipin antibodies have been determined in a series of thrombotic patients both by an ELISA technique and by the method of the invention. As seen in FIG. 7, the method of the invention provides comparable sensitivity to presently available ELISA techniques.

The assay methods have been described with reference to serum but it will be understood by those skilled in the art that plasma may be similarly assayed.

In accordance with a further embodiment of the invention, a convenient and rapid method is provided for isolating antiphospholipid antibodies.

A solution containing antiphospholipid antibodies to be isolated is mixed with microspheres coated with the appropriate phospholipid or phospholipids and blocked as in Example 1, and the mixture is stirred at about 0° C. for one hour. The beads are pelleted by centrifugation and washed twice with 0.01M Tris, 0.14M NaCl (pH 7.35) containing 10% v/v fetal calf serum. The beads are washed once with 0.01M Tris, 0.14M NaCl (pH 7.35) and centrifuged to a pellet. The bound antibodies are eluted with a chaotropic salt such as KI, KSON or NaI (1M) with incubation at room temperature for 1 hour. The phospholipid beads are then removed by centrifugation and the eluted antibodies subjected to further purification on a Protein A column or hydrazide column composed of antibodies to the desired immunoglobulin subclass.

In accordance with a further embodiment of the invention, a method is provided for raising antibodies to a phospholipid.

Various immunisation schemes have been employed to raise antibodies to phospholipids but these have generally yielded non-specific antibodies.

The phospholipid coated microspheres of the invention present phospholipid antigens in such a way that they can bind to their specific antibodies. Administration of these phospholipid microspheres to an animal, for example by subcutaneous injection, conveniently presents the animal's immune system with a phospholipid antigen against which specific antibodies are elicited. The coated microspheres present a large surface area displaying antigen and adapted to elicit a good immunological response. The microspheres are coated with phospholipid as in Example 1 but are not treated with blocking agent.

In accordance with a further embodiment, kits for determining antiphospholipid antibodies are provided comprising phospholipid coated particles and one or more labelled reagents capable of binding to the antiphospholipid antibodies.

The following examples are given for the purpose of illustrating the invention and the present invention is not limited thereto.

Materials

The following materials were purchased from Sigma Chemicals (St. Louis, Mo.): phosphatidylinositol, phosphatidylserine, cardiolipin, goat anti-human IgG F(ab')$_2$ linked to fluoresceinisothyocyanate (FITC), tris (hydroxymethyl) methylamine, sodium chloride. Heat inactivated fetal calf serum was purchased from GIBCO (Burlington, Ont.). Avidin linked to PE/Texas Red was purchased from Southern Biotechnology (Birmingham, Ala.). Polystyrene microspheres (beads) were purchased from PolySciences (Warrington, Pa.). Absolute ethanol was produced by triple distillation of stock ethanol purchased from BDH (Edmonton, Alta). Chloroform and methanol were purchased from BDH (Edmonton, Alta). Isoton II was purchased from Coulter Electronics (Hialeah, Fla.). Flow cytometric analysis was performed on a FACScan from Becton Dickinson (Mountainview, Calif.). Antiphospholipid antibody standards were purchased from Antiphospholipid Antibody Associates (Louisville, Ky.).

EXAMPLE 1

Phospholipid Preparation

Cardiolipin (CL) was supplied as a 5 mg/mL solution in ethanol and used without further modification. Phosphatidylinositol (PI) was initially dissolved in chloroform:methanol (99:1) then further diluted in absolute ethanol to produce a stock solution of 10 mg/mL. Phosphatidylserine (PS) was initially dissolved in chloroform:methanol (95:1) then further diluted in absolute ethanol to produce a stock solution of 25 mg/mL. All solutions were stored in the dark at 4° C.

Pre-treatment of Microspheres

Polystyrene microspheres (beads) of defined size were supplied by the manufacturer in sterile distilled water. Prior to coating with phospholipid, the beads were washed several times with distilled water followed by several washes in absolute ethanol. Washing was accomplished by centrifugation. All ethanol washes and subsequent manipulation of beads should be carried out in glass vessels using glass transfer implements.

Coating Procedure

After washing, beads were resuspended to a final volume of 1 mL in absolute ethanol.

Beads of three different sizes were coated with three different phospholipids; beads of average diameter 5.8 μm (±0.1 μm) were coated with CL, beads of 2.9 μm (±0.1 μm) with PS and beads of 1.6 μm (±0.1 μm) with PI.

The polystyrene bead number was adjusted so that the surface area presented by each size of bead to be coated was the same. In a like manner, the phospholipid concentrations were adjusted to provide approximately similar amounts by weight per unit area of bead. Table 1 shows an example of suitable coating parameters.

TABLE 1

| PHOSPHOLIPIDS (BEAD DIAMETER) | PI (1.6 μm) | PS (2.9 μm) | CL (5.8 μm) |
| --- | --- | --- | --- |
| Particles per mL | 1.11 × 10$^{10}$ | 0.18 × 10$^{10}$ | 0.02 × 10$^{10}$ |
| Particles coated (100 μm) | 11.1 × 10$^8$ | 1.80 × 10$^8$ | 2.00 × 10$^8$ |
| Surface Area (×10$^{10}$ μm$^2$) | 0.89 | 0.48 | 0.22 |
| Coating Volume | 40 μL | 9 μL | 20 μL |
| Phospholipid Conc. (Stock solution) | 10 mg/mL | 25 mg/mL | 5 mg/mL |
| Coating/Unit Area (mg/10$^{10}$ μm$^2$) | 0.45 | 0.47 | 0.45 |

The volumes of phospholipid indicated in Table 1 (relative phospholipid concentrations also given in Table 1) were added to the bead suspensions and mixed by aspiration. The bead suspensions were sealed and incubated overnight at 4° C. in the dark.

The phospholipid coated beads were then treated with a blocking agent to reduce non-specific binding of immunoglobulins and other potentially interfering proteins. Phospholipid coated beads in ethanol were allowed to come to room temperature and were washed by mixing gently by aspiration with an equal volume of Tris/NaCl buffer (0.01M Tris, 0.14M NaCl, pH 7.2), followed by centrifugation. After a further two washes with buffer, the beads were resuspended in "blocking solution" (500 μL), i.e. 10% v/v fetal calf serum in 0.01M Tris, 0.14 NaCl, pH 7.2, and incubated at 37° C. for 30 minutes followed by rapid cooling at 0° C.

Once the phospholipid-coated beads have been blocked, it is no longer necessary to use glass transfer implements and glass vessels. Reactions are conveniently carried out in 1.5 mL polypropylene microfuge tubes.

The un-blocked phospholipid coated beads may be stored for later use before treatment with the blocking agent. Various storage conditions were examined, using cardiolipin coated beads, and some examples of suitable storage conditions are shown in Table 2.

TABLE 2

| STORAGE CONDITIONS | STORAGE TIME | BETWEEN RUN CV |
|---|---|---|
| 4° C., in Phospholipid/ EtOH Solution, in Dark | 4 months | 7% (N = 10) |
| −20° C., freeze dried, in dark | 4 months | 10% (N = 10) |
| −20° C., in glycerol, in dark | 2 months | 15% (N = 7) |

EXAMPLE 2

Beads of three sizes were coated with CL, PS and PI as described in Example 1 and mixed in the proportions 1 part 1.6 µm beads: 2 parts 2.9 µm beads:4 parts 5.8 µm beads, based on the number of particles coated for each bead size as in Table 1. The bead mixture was suspended in blocking solution.

For assay, 5 µL of serum to be analysed was mixed with 495 µL bead mixture suspension and incubation was carried out at 0° for 60 minutes. Unbound immunoglobulins and other contaminating proteins were removed from the beads by centrifugation and the beads were resuspended in a secondary antibody mixture containing goat anti-human IgG-FITC F(ab')$_2$, goat anti-human IgM-PE and goat anti-human IgA-biotin. Saturating concentrations of antibodies were used, as determined by titration. After a 30 minute incubation at room temperature, the beads were separated from unbound antibodies by centrifugation and resuspended in saturating concentrations of avidin linked to PE/Texas red, with incubation at room temperature in the dark for 15 minutes. Beads were again separated by centrifugation and resuspended in balanced salt solution, ISOTON II™ (Coulter Electronics).

Resuspension volumes of 0.5 to 1.0 mL were employed for use with a FACScan flow cytometer for analysis. The resuspended beads were transferred to 12×75 mm polystyrene tubes and analyzed by standard flow cytometric methods. The flow cytometer was capable of measuring five (5) separate parameters on each particle examined. Forward scatter 180° relative to the incident laser light (488 nm), indicated the size of the particle. Side scatter, 90° relative to the incident laser, indicated internal complexity of the particle. In addition three different fluorescence parameters, based on emission spectra (post excitation with 488 nm laser), were analyzed. Spectral overlap by the three available fluorescent tags (FITC, PE, PE/Texas Red) was compensated for electronically as outlined by the manufacturer. All data was stored to disk in list-mode. Subsequently, the data were analyzed for each bead size based on electronically selecting (gating) each bead population and analyzing the fluorescence exhibited.

The machine was calibrated daily using fluorescent microparticles (Calibrite Beads, Becton Dickinson) and compensation for interchannel bleeding was set for three colour analysis where more than one labelled antibody was measured.

The excellent discrimination between the three bead sizes coated with PI, PS and CL respectively is shown in FIG. 1, a forward scatter histogram.

EXAMPLE 3

Sera to be screened were diluted with bead mixture suspension as in Example 2 and incubated at 0° C. for 60 minutes.

A saturating concentration of goat anti-human polyvalent (IgA, IgM, IgG) antiserum labelled with FITC was added directly to the serum/bead mixture, without separation of beads from test serum and incubation was carried out at room temperature in the dark for 30 minutes.

A negative control and a positive control were included in each analysis as a check on run to run reproducibility.

After incubation, the incubation mixture was diluted about 30-fold with saline and was directly analysed by flow cytometry as in Example 2.

EXAMPLE 4

For quantitation of serum antibodies of a particular immunoglobulin class directed against a specific phospholipid, test sera were analysed by the procedure described in Example 2 employing beads of one size coated with the appropriate phospholipid and using as secondary antibody FITC or PE labelled goat anti-human antibodies against IgM or IgA, or goat anti-human IgG-FITC F(ab')$_2$.

Standard curves were prepared using antiphospholipid antibody standards obtained from Antiphospholipid Antibody Associates. The peak mean channel fluorescence was plotted logarithmically against the log of the antiphospholipid antibody concentration (in GPL, MPL or APL units).

Concentration of antiphospholipid antibody was expressed as immunoglobulin binding units to phospholipid, abbreviated as GPL, MPL and APL for IgG, IgM and IgA bound to phospholipid respectively.

The immunoglobulin binding units were defined by Harris et al (Clin. Exp. Immunol., 69: 215, 1987) to be the phospholipid binding activity of 1 µg/mL of an affinity purified IgG (GPL), IgM (MPL) or IgA (APL) preparation from a standard serum.

Figure 3:
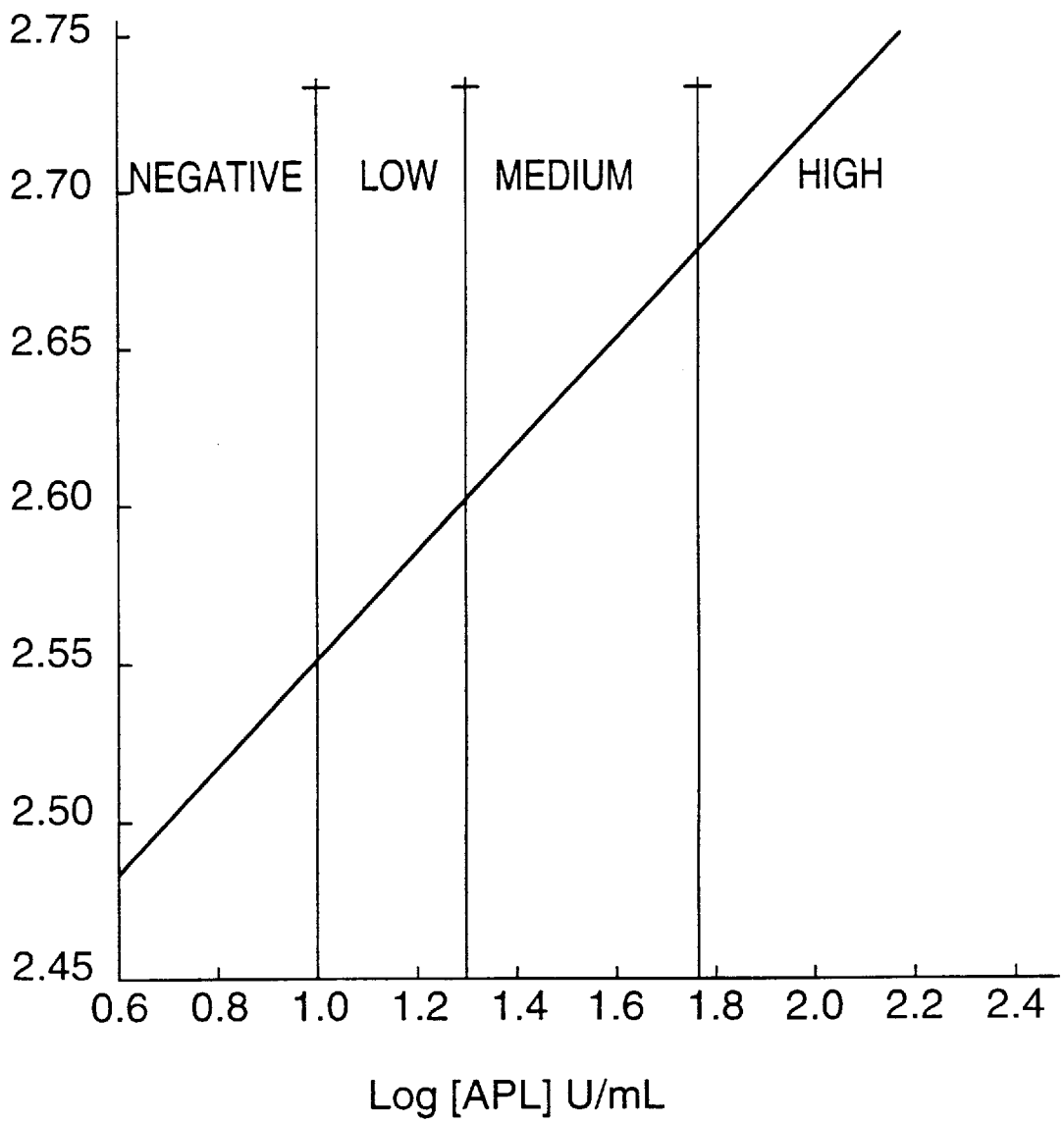
FIG. 3 is a standard curve in APL units.
Figure 4:
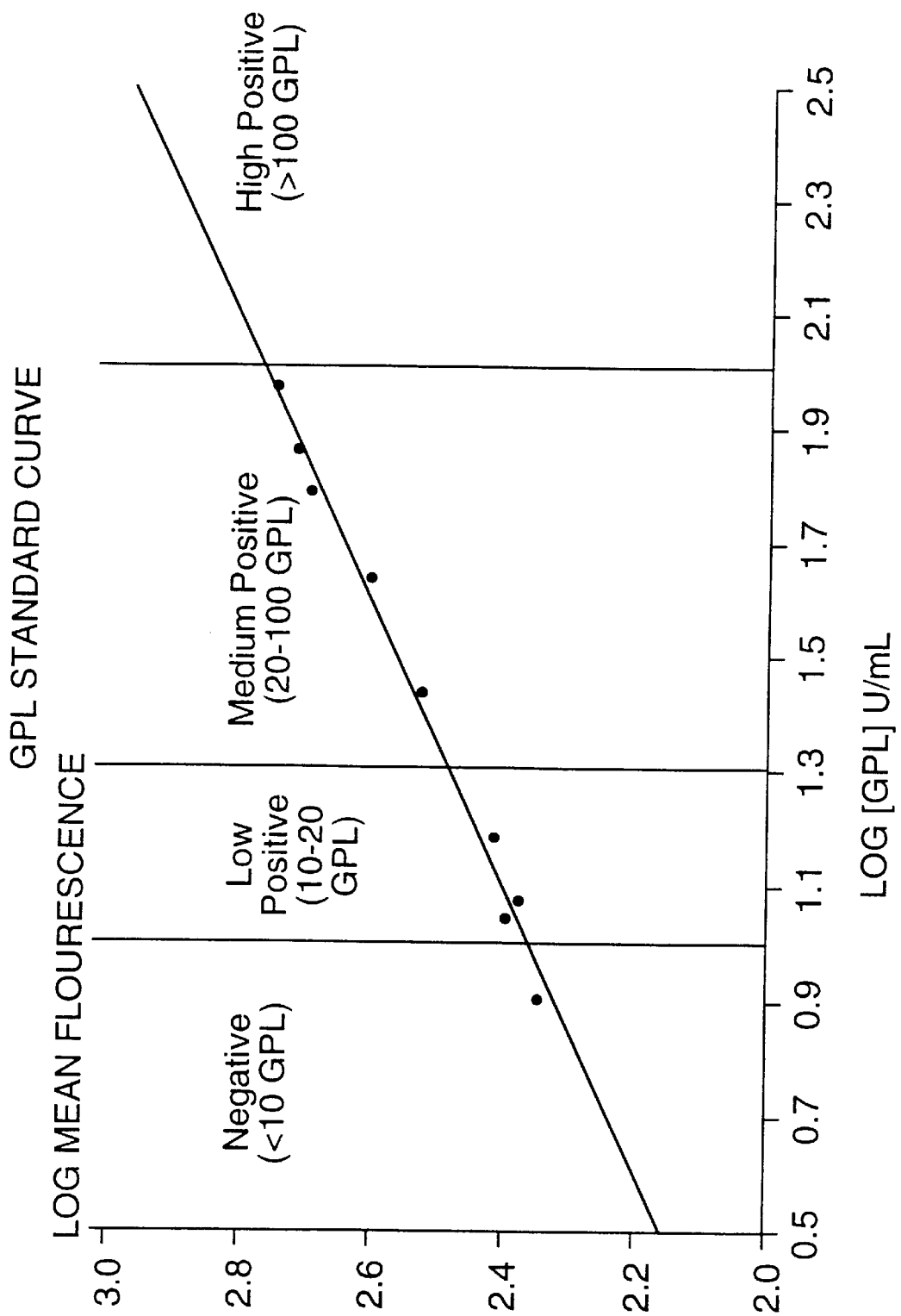
FIG. 4 is a standard curve in GPL units.

Examples of standard curves generated are shown in FIGS. 3 and 4.

EXAMPLE 5

Figure 5:
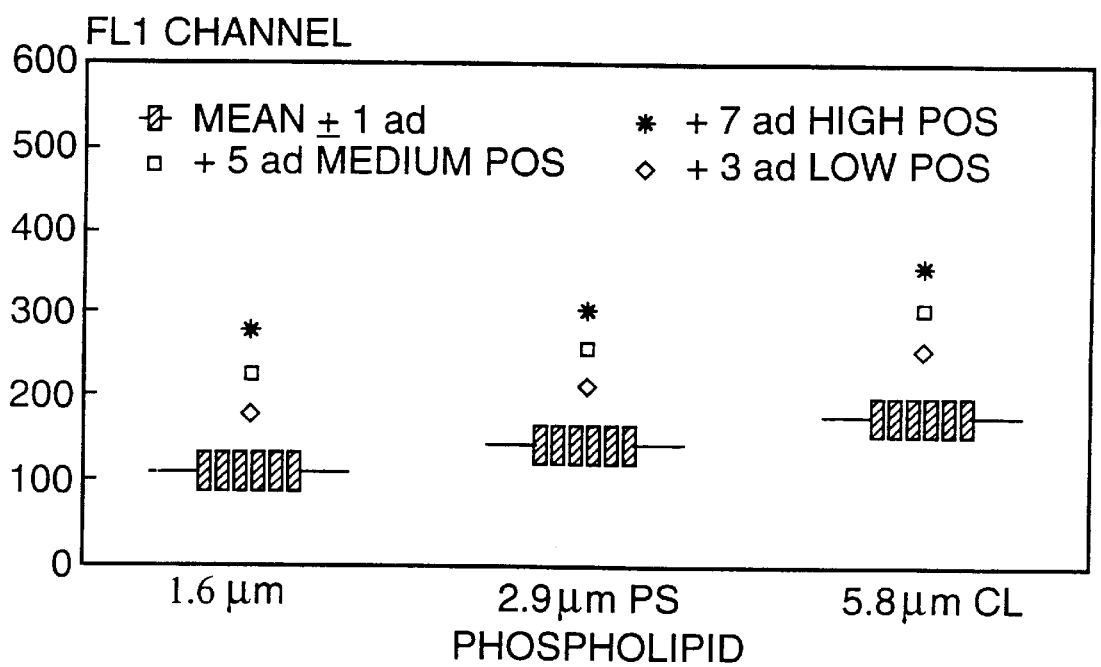
FIG. 5 shows normal ranges of antiphospholipid antibodies in human serum, determined by the method of the invention.

Serum samples were obtained from 26 healthy volunteers and levels of antiphospholipid antibodies to PI, PS and CL were measured as in Example 4. Polyvalent secondary antibodies were employed, giving a measure of total IgG, IgM and IgA against each phospholipid. The results obtained are shown in FIG. 5.

EXAMPLE 6

Serum samples were obtained from eight patients with a history of thrombotic episodes. An initial screen was performed by the procedure of Example 2 to determine the immunoglobulin class and phospholipid specificity of any antiphospholipid antibodies present. Each type of antiphospholipid antibody detected by the screen was then quantitated as described in Example 4. Antibodies to one or more phospholipids were found in seven of the eight patients, as seen in FIG. 6. The results are presented as negative, low positive, medium positive and high positive as recommended by Harris et al (Clin, Exp. Immunol., 68: 215, 1987). The degree of positivity was based on the number of standard deviations above the normal ranges of 26 normal controls as follows: Negative≦3 sd, Low Positive=between 3 and 5 sd, Medium Positive=between 5 and 7 sd and High Positive>7 sd; as regards mean channel fluorescence.

EXAMPLE 7

A comparison was made of serum anti-cardiolipin antibody levels determined by the method of the invention and those obtained by the ELISA method of Loizou et al (Clin. Exp. Immunol., (1985) vol. 62, pp 738–745). Sera examined were obtained from 30 patients with thrombotic tendencies.

After screening the sera as in Example 2 for the presence of anti-cardiolipin antibodies, levels of GPL were determined in positive sera by the procedure of Example 4. Binding of GPL was assessed and GPL values were determined based on the cut-off values recommended by Antiphospholipid Antibody Associates. For the ELISA method, the secondary antibody used was goat anti-human IgG linked to peroxidase. The results are shown in FIG. 7.

Although only certain embodiments of the present invention have been described and illustrated, the present invention is not limited to the features of these embodiments, but includes all variations and modifications within the scope of the claims.

We claim:

1. A method for determining the presence, in a fluid, of anti-target-phospholipid antibodies, comprising:
    contacting microspheres with a solution of a target phospholipid, which is selectively bound by antibodies to be determined, under conditions effective to allow coating of the phospholipid on the microspheres thereby forming a solution/phospholipid-coated microsphere mixture;
    washing the phospholipid-coated microspheres by mixing the solution/phospholipid-coated microsphere mixture with an equal volume of aqueous buffer and collecting the washed phospholipid-coated microspheres;
    contacting a fluid suspected of containing anti-target-phospholipid antibodies with the phospholipid-coated microspheres to permit binding of any anti-target-phospholipid antibodies present in the fluid to the phospholipid-coated microspheres; and
    determining the presence of any anti-target phospholipid antibodies bound to the phospholipid-coated microspheres.

2. The method of claim 1, wherein the microspheres comprise beads.

3. The method of claim 1, wherein the microspheres are selected from the group consisting of polypropylene, polyethylene, acrylonitrile, polystyrene, polycarbonate, and nitrocellulose.

4. The method of claim 1, wherein the microspheres comprise latex microspheres.

5. The method of claim 1, wherein the microspheres comprise magnetic microspheres.

6. The method of claim 1, wherein the phospholipid is selected from the group consisting of cardiolipin, phosphatidyl inositol, phosphatidyl serine, phosphatidic acid, and phosphatidyl ethanolamine, and mixtures of the phospholipids.

7. The method of claim 1, wherein the fluid is a biological fluid.

8. The method of claim 7, wherein the biological fluid comprises serum or plasma.

9. The method of claim 8, wherein the serum or plasma comprises human serum or plasma.

10. The method of claim 1, wherein any anti-target-phospholipid antibodies bound to the phospholipid-coated microspheres are determined with a detectably-labeled reagent which binds to the anti-target-phospholipid antibodies.

11. The method of claim 10, wherein the detectably-labeled reagent comprises detectably-labeled polyvalent anti-human immunoglobulin antiserum.

12. The method of claim 10, wherein the detectably-labeled reagent comprises at least one anti-human monovalent antibody or binding fragment thereof directed against at least one immunoglobulin class.

13. The method of claim 10, wherein the detectably-labeled reagent comprises a detectable label attached to anti-immunoglobulin antibodies or binding fragments thereof selected from the group consisting of anti-human IgG, anti-human IgM and anti-human IgA antibodies and the presence of any anti-target-phospholipid antibodies is determined as anti-phospholipid IgG, IgM or IgA antibodies.

14. The method of claim 10, wherein the detectably-labeled reagent comprises a detectable label attached to anti-immunoglobulin antibodies or binding fragments thereof selected from the group consisting of anti-human IgG F(ab')$_2$, anti-human IgA and anti-human IgM and the presence of any anti-target-phospholipid antibodies is determined as anti-phospholipid IgG, IgM or IgA antibodies.

15. The method of claim 14, wherein the detectably-labeled reagent comprises anti-human IgG F(ab')$_2$-FITC, anti-human IgM-phycoerythrin and anti-human IgA-biotin, and the method further comprises contacting the microspheres with avidin-Texas red to permit binding to the biotin.

16. The method of claim 1, wherein the anti-target-phospholipid antibodies comprise anti-target-phospholipid antibodies associated with arterial and venous thrombosis, recurrent fetal loss, thrombocytopenia, pulmonary embolism, coronary thrombosis, cerebral thrombosis, livedo reticularis or HIV infection.

17. A method for separately determining the presence, in a fluid, of at least two different anti-target-phospholipid antibodies which selectively bind different target phospholipids, comprising:
    obtaining microspheres of at least two size classes;
    separately contacting each microsphere class with a solution of a different target phospholipid that is selectively bound by antibodies to be determined, under conditions effective to allow coating of each microsphere class with a different target phospholipid, thereby forming at least two different solution/phospholipid-coated microsphere mixtures;
    washing each microsphere class by mixing each solution/phospholipid-coated microsphere mixture with an equal volume of aqueous buffer and collecting each of the washed phospholipid-coated microsphere classes;
    contacting a fluid suspected of containing anti-target-phospholipid antibodies with a mixture comprising phospholipid-coated microspheres from each of the at least two classes, and allowing any anti-target-phospholipid antibodies present in the fluid to bind to the phospholipid-coated microspheres; and
    determining the presence of any anti-target-phospholipid antibodies bound to each phospholipid-coated microsphere class.

18. The method of claim 17, wherein the fluid comprises a biological fluid.

19. The method of claim 18, wherein the biological fluid comprises serum or plasma.

20. The method of claim 19, wherein the serum or plasma comprises human serum or plasma.

21. The method of claim 17, wherein any anti-target-phospholipid antibodies bound to each phospholipid-coated microsphere class are separately determined by flow cytometry with a detectably-labeled reagent, which binds to the at least two different anti-target-phospholipid antibodies.

22. The method of claim 21, wherein
the microsphere classes comprise first, second and third microsphere size classes;
the first class comprises microspheres of about 1.6 μm average diameter;
the second class comprises microspheres of about 2.9 μm average diameter;
the third class comprises microspheres of about 5.8 μm average diameter; and
each microsphere class is coated with a different target phospholipid selected from the group consisting of cardiolipin, phosphatidyl inositol, phosphatidyl serine, phosphatidic acid and phosphatidylethanolamine.

23. The method of claim 22, wherein the detectably-labeled reagent comprises a separately-detectable label attached to anti-immunoglobulin antibodies selected from the group consisting of anti-human IgG F(ab')$_2$, anti-human IgM and anti-human IgA and the presence of any anti-target-phospholipid antibodies is determined as anti-phospholipid IgG, IgM or IgA antibodies.

24. The method of claim 17, wherein the anti-target-phospholipid antibodies determined comprise anti-target-phospholipid antibodies associated with arterial and venous thrombosis, recurrent fetal loss, thrombocytopenia, pulmonary embolism, coronary thrombosis, cerebral thrombosis, livedo reticularis or HIV infection.

25. A method for determining the amount, in a fluid, of anti-target-phospholipid antibodies, comprising:

(a) contacting microspheres with a solution of a target phospholipid, which is selectively bound by antibodies to be determined, under conditions effective to allow coating of the phospholipid on the microspheres thereby forming a solution/phospholipid-coated microsphere mixture;

(b) washing the phospholipid-coated microspheres by mixing the solution/phospholipid-coated microsphere mixture with an equal volume of aqueous buffer, and collecting the washed phospholipid-coated microspheres;

(c) separately contacting at least two portions of the phospholipid-coated microspheres with at least two known amounts of standard anti-target-phospholipid antibodies to permit binding of the standard anti-target-phospholipid antibodies to the phospholipid-coated microspheres, and contacting the standard anti-target-phospholipid antibodies bound to the phospholipid-coated microspheres with a detectably-labeled reagent which binds to anti-target-phospholipid antibodies to provide a standard curve;

(d) contacting a fluid suspected of containing anti-target-phospholipid antibodies with a further portion of phospholipid-coated microspheres to permit binding of any anti-target-phospholipid antibodies present in the fluid to the phospholipid-coated microspheres and contacting any anti-target-phospholipid antibodies bound to the phospholipid-coated microspheres with the detectably-labeled reagent which binds to anti-target-phospholipid antibodies; and (e) determining the amount of anti-target-phospholipid antibodies present in the fluid by comparing the amount of detectably-labeled reagent bound to the phospholipid-coated microspheres of step (d) with the standard curve of step (c).

* * * * *